United States Patent [19]

Lin

[11] 4,284,619
[45] Aug. 18, 1981

[54] ESTERS USEFUL AS BRAIN IMAGING AGENTS

[75] Inventor: Tz-Hong Lin, Fremont, Calif.

[73] Assignee: Medi-Physics, Inc., Emeryville, Calif.

[21] Appl. No.: 964,563

[22] Filed: Nov. 29, 1978

[51] Int. Cl.³ .................... A61K 49/00; A61K 43/00; C07C 69/76
[52] U.S. Cl. ........................................ 424/1.5; 424/9; 424/1; 560/8; 560/106
[58] Field of Search ............... 560/8, 103, 106; 424/1, 424/1.5, 9

[56] References Cited

U.S. PATENT DOCUMENTS

| | | | |
|---|---|---|---|
| 3,144,479 | 8/1964 | Obendorf | 560/103 |
| 3,317,569 | 5/1967 | Larsen et al. | 560/103 |

OTHER PUBLICATIONS

Tubis et al., Int. J. Appl. Rad. Isot., 15:397–400, (1964).
Elias et al., Int. J. Appl. Rad. Isot., 24:463–469, (1973).
Blav et al., Int. J. Appl. Rad. Isot., 3:217–225, (1958).
Hansen et al., J. Med. Chem., 21:830–833, (1978).

Holman et al., T. Lab. Comp. Radiopharm, 16:69–71, (1979).

*Primary Examiner*—Brooks H. Hunt
*Assistant Examiner*—Christine M. Nucker
*Attorney, Agent, or Firm*—Jon S. Saxe; George M. Gould; William H. Epstein

[57] ABSTRACT

Certain radioiodine containing esters useful as brain imaging agents are disclosed. The compounds of the subject invention are represented by the formula

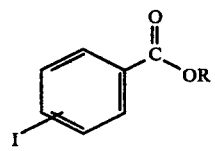

wherein I is a radioisotope of iodine with iodine-123 being preferred and R is selected from the group consisting of alkyl, aryl, substituted aryl, aralkyl, a polyhydric alcohol radical and a 5- or 6-membered heterocyclic ring.

6 Claims, No Drawings

ESTERS USEFUL AS BRAIN IMAGING AGENTS

STATEMENT OF PRIOR ART

The use of radioiodine to label organic compounds for use in diagnostic nuclear medicine is well documented in the literature. Radioiodinated human serum albumin, fatty acids and triglycerides as well as ortho-iodohippuric acid have long been available for diagnostic purposes. The preparation of I-131-labeled ortho-, meta- and paraiodobenzoic acids for liver function procedures is described by Tubis et al., Int. J. Applied Radio Isotopes 15, p. 397 (1964).

The use of the N-hydroxysuccinimide ester of 3-(4-hydroxyphenyl)propionic acid I-125 to radiolabel proteins is reported by Bolton and Hunter, Biochem J. 133, pp. 529–539 (1973). Smith, U.S. Pat. No. 3,979,506 describes imido esters of radionuclide-substituted hydroxy or alkoxy phenyls wherein the nuclide can be, for example I-125.

The use of p-iodobenzoyl chloride (I-131) to label antibodies for the determination of in vivo protein distribution is reported by Blau et al., Intern. J. Appl. Radiation and Isotopes 3, pp. 217–225 (1958).

Stokes et al. have reported on the chromatography of I-131 labeled esters of, e.g., cholestanol and 7-dehydrocholestanol in the Journal of the American Chemical Society, 76, pp. 5174–5175 (1954). No utility was given for the disclosed esters.

BACKGROUND OF THE INVENTION

As will be appreciated from the foregoing literature references, the art has long been appraised of the use of radio-iodine labeled compounds in nuclear medical diagnostic procedures. The art has further been appraised of increasing interest in finding compounds which will effectively cross the blood/brain barrier, thus facilitating more efficacious imaging of the brain.

The compounds of the subject invention facilitate a means whereby a radionuclide is able to efficiently cross the blood/brain barrier. Specifically, the compounds of the present invention facilitate the rapid passage of a radioisotope of iodine, preferably I-123, across the blood/brain barrier. I-123 is preferred because it compares very favorably with I-131 in terms of half-life and absorbed radiation dose.

Because the half-life of I-123 is only 13 hours, it is necessary that procedures in labeling compounds with this radionuclide be both rapid and efficient. It is further necessary, as with any radiolabeled compounds, that the radiolabel, i.e., the iodinecarbon bond in the case of the subject compounds, be stable in vivo with minimal loss of radionuclide from the labeled compound after its administration to the patient. The compounds provided by the present invention satisfy all of these requirements.

DETAILED DESCRIPTION OF THE INVENTION

The present invention is directed to radioiodinated esters represented by the formula

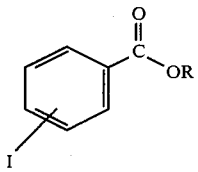

wherein I is a radioisotope of iodine and R is selected from the group consisting of alkyl, aryl, substituted aryl, aralkyl, a polyhydric alcohol radical and a 5- or 6-membered heterocyclic ring.

The compounds of formula A are useful for imaging of the brain. The compounds of the invention demonstrate rapid accumulation in the brain indicating ability to penetrate the "blood-brain barrier". In comparison to I-123 labeled 4-iodoantipyrine which has been described in the art by Robinson et al, J. Nucl. Med. 17, p 1093 (1976) as a brain imaging agent, the compounds of formula A are comparable in stability of the iodine-carbon bond. In addition to imaging of the brain, the compounds of formula A also demonstrate localization in the heart, the adrenals and the pancreas.

The compounds of formula A show rapid accumulation in the brain after intravenous administration without the significant loss of the iodine label in the brain which has been shown to be a disadvantage of prior art brain imaging agents such as I-123 4-iodoantipyrine. The stability of the iodine label in the compound combined with the ability to pass the blood/brain barrier are distant advantages of the compounds of formula A in their use as brain imaging agents.

As utilized herein, the term "alkyl" indicates a straight- or branched-chain radical having 1 to 18 carbon atoms such as, for example, methyl, ethyl, isopropyl, n-octadecyl and the like. The ethyl radical is preferred. The term "aryl" indicates an aromatic mononuclear or polynuclear hydrocarbon radical such as, for example, phenyl, naphthyl and phenanthryl, with phenyl being preferred. The alkyl portion of "aralkyl" as utilized herein indicates a straight-chain alkyl having from 1 to 6 carbon atoms. A preferred aralkyl radical in accordance with the present invention is benzyl.

The terminology "substituted aryl" as utilized herein indicates an aryl radical substituted with lower alkyl, i.e., a straight-chain alkyl radical having from 1 to 6 carbon atoms, alkoxy, hydroxy or halogen. The alkyl portion of the alkoxy radical is a lower alkyl radical as defined above. Preferred substituted aryls include 2,6-dimethylphenyl and pyrogallyl. By "halogen" is meant chloro, bromo or trifluoromethyl. Examples of polyhydric alcohol radicals in accordance with the invention include glyceryl, sorbityl, glucosyl and the like. The 5- or 6-membered heterocyclic rings designated by R in formula A include, for example, pyrrolidino, pyridino, piperidino, morpholino, thiomorpholino with pyridoxyl being preferred.

As stated above, "I" indicates all radioisotopes of iodine, e.g., I-123, I-125 and I-131. Of these, I-123 is particularly preferred in the practice of the invention.

Preferred compounds in accordance with the present invention include I-123-ethyl-o-iodobenzoate; I-123-glyceryl-o-iodobenzoate and I-123-benzyl-o-iodobenzoate.

The radioiodinated compounds of the present invention are prepared by reacting a compound represented by the formula

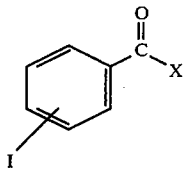

wherein I is as defined above and X is chloro, bromo or hydroxy with a compound represented by the formula

HO—R     C wherein R has the meaning given above.

For the above reaction, the compound of formula B is conveniently dissolved in an inert organic solvent such as, for example, ethyl acetate, dioxane, methylene chloride, benzene, dimethylformamide, tetrahydrofuran and the like with the latter being preferred. The alcohols of formula C may be in aqueous solution if they are of low molecular weight and sufficiently soluble to do so or, in the alternative, may be in solution in an inert, organic solvent such as those named above. The reaction is usually carried out at ambient temperatures although gentle heating may be preferred in certain instances. The reaction is generally rapid requiring from about 5 minutes to about 60 minutes. The product is recovered by conventional procedures.

Alternatively, compounds of formula A wherein the I does not indicate a radioisotope of iodine, i.e., the corresponding cold compound, may be prepared as described above utilizing compounds of formula B wherein I is stable iodine and not a radioisotope of iodine under the same conditions. These compounds are then exchange labeled with a radioisotope of iodine, preferably I-123.

For the exchange radiolabeling process, an inorganic salt of a radioisotope of iodine, preferably an alkali metal salt and most preferably the sodium salt, is utilized. The salt is heated with the cold compound of formula A, i.e., a compound of formula A wherein I is stable iodine and not a radioisotope of iodine, in a sealed vessel for from ¼ to about 2 hours. The exchange radiolabeling is carried out in the presence of an inert organic solvent such as, for example, a lower alcohol or those named above. The radiolabeled compound of formula A is then dissolved in a suitable solvent or vehicle and filtered through a silver chloride impregnated filter to remove unexchanged radioiodine. The exchange labeling carried out in this manner has been demonstrated to be in excess of 95%.

The compounds of formula B above can be prepared conveniently from the corresponding cold compound, i.e., a compound of formula B wherein I represents stable iodine as opposed to a radioisotope of iodine by exchange radio labeling as described above. The cold compounds of formula B are known.

The rapidity of preparation of the compounds of formula A is advantageous because of the criticality of time in the handling of radioisotopes which have a comparatively short half life such as iodine-123.

As stated above, the radioiodine containing compounds of the invention rapidly localize in the brain following intravenous administration. In most instances, a sufficient amount of the administered dose will accumulate in the brain within from about one to ten minutes to permit the taking of scintiphotos. The compounds of the invention will show meaningful presence in the brain for up to about 30 minutes so that significant studies may be carried out. The compounds of formula A clear the brain within a relatively short period of time and are excreted through the kidneys. In addition to the brain, the compounds of formula A will also accumulate in the myocardium, adrenals and pancreas to varying degrees.

The radioiodinated compounds of the subject invention may be administered in an aqueous or aqueous/alcoholic medium. Such media may also contain conventional pharmaceutical adjunct materials such as, for example, pharmaceutically acceptable salts to adjust the osmotic pressure, buffers, preservatives and the like.

A preferred vehicle for the compounds of formula A comprises from about 20% to about 70%, preferably from about 25% to about 45%, propylene glycol, from about 1% to about 40%, preferably from about 5% to about 30%, ethanol, from about 1% to about 5% of a complexing agent such as, for example, ethylenediaminetetraacetic acid, a suitable buffer such as, for example, a mixture of acetic acid and sodium acetate, from about 0.5% to about 2% of a suitable preservative and the remainder water. Preferred preservatives include, for example, benzyl alcohol, phenol, esters of para-hydroxy benzoic acid and the like.

The following examples further illustrate the invention. Unless otherwise noted, all temperatures are in degrees Centigrade.

EXAMPLE 1

One ml. of o-iodobenzoyl chloride and 5 ml. of methyl alcohol were reacted at room temperature. The resulting mixture was taken up in 50 ml. of ether. The ether solution was washed with three 50 ml. portions of 1 N sodium hydroxide and then with deionized water until the washings were neutral. Evaporation of the ether solution yielded 1.2 g. of liquid methyl o-iodobenzoate, $R_f$ value of 0.76 on thin layer chromatography using silica gel 60 and methanol-chloroform-acetic acid (15:18:1).

EXAMPLE 2

Ten ml. of ethyl alcohol was reacted with 1 ml. of o-iodobenzoyl chloride according to the procedure of Example 1. There was obtained 1.5 g. of liquid ethyl o-iodobenzoate, $R_f$ 0.82. The gas liquid partition chromatography retention time of the product on 3% SE-30* (10'×⅛", 25 ml/min.) at 230° was 5 minutes.

*A methyl silicone polymer manufactured by General Electric Company.

EXAMPLE 3

Five ml. of isopropyl alcohol was reacted with 1 ml. of o-iodobenzoyl chloride in accordance with the procedure of Example 1. There was obtained 1.07 g. of liquid isopropyl o-iodobenzoate, $R_f$ 0.77.

EXAMPLE 4

Five ml of 1,2-propylene glycol was reacted with 1 ml of o-iodobenzoyl chloride in accordance with the procedure of Example 1. There was obtained 1.1 g of liquid hydroxypropyl o-iodobenzoate. The product was shown by TLC to be a mixture of two isomers having $R_f$ values of 0.8 and 0.68, respectively.

EXAMPLE 5

Five ml of glycerin was reacted with 1 ml of benzoyl chloride in accordance with the procedure of Example 1. There was obtained 0.75 g of glyceryl o-iodobenzoate as a viscous liquid. The product was shown by TLC to be a mixture of three isomers having $R_f$ values of 0.86, 0.72, and 0.54, respectively.

EXAMPLE 6

Five ml of phenol was reacted with 1 ml of o-iodobenzoyl chloride in accordance with the procedure of Example 1. There was obtained 1.86 g of liquid phenyl o-iodobenzoate, $R_f$ 0.75. The gas liquid partition chromatography retention time of the product on 3% SE-30 (10'×⅛", 25 ml/min.) at 275° was 5.8 minutes.

EXAMPLE 7

Two ml of o-iodobenzoyl chloride was reacted with ten ml of benzyl alcohol in accordance with the procedure of Example 1. There was obtained 2.26 g of liquid benzyl o-iodobenzoate, $R_f$ 0.79. The gas liquid partition chromatography time of the product on 3% SE-30 (10'×⅛", 30 ml/min.) at 200° was 14.6 minutes.

EXAMPLE 8

A total of 1.26 g of pyrogallol and 1 ml of o-iodobenzoyl chloride were melted over slow heat and allowed to stand at ambient temperature overnight. The reaction mixture was then taken up in 50 ml of methyl alcohol. The precipitate which appeared after the methyl alcohol solution was allowed to stand was collected by filtration. There was thus obtained 0.35 g of pyrogallyl o-iodobenzoate, mp 140°–145°.

EXAMPLE 9

Fifty ml of ether and 100 ml of deionized water were combined and 2 g of pyridoxine hydrochloride and 1 ml of o-iodobenzoyl chloride were added thereto. The pH of the aqueous phase was adjusted to pH 9 by the addition of about 1 ml of 50% sodium hydroxide with stirring. The solution was stirred for an additional hour. The precipitate which formed was recovered and recrystallized from a mixture of water and acetone to yield 1.99 g of pyridoxyl o-iodobenzoate, mp 135°, $R_f$ 0.73.

EXAMPLE 10

One ml of o-iodobenzoyl chloride was reacted with 2.7 g of 1-octadecanol in accordance with the procedure of Example 8. There was obtained 2.36 g of octadecyl o-iodobenzoate, mp 35°, $R_f$ 0.66.

EXAMPLE 11

The radioiodine-containing compounds analogous to those prepared in Examples 1 through 10 were prepared as follows, utilizing ethyl o-iodobenzoate prepared in Example 2 for illustration.

A solution of 53.7 mCi carrier-free sodium iodide I-123 in 0.1 ml of ethanol was evaporated to dryness in a test tube. A solution of 0.05 ml of 0.1 Methyl-o-iodobenzoate in ethanol was added and the walls of the tube were rinsed with 20 microliters of ethanol. The open end of the tube was sealed with a torch and the sealed tube heated in an autoclave at 121° for one hour. The tube was then allowed to cool. An aliquot of the product was analyzed by TLC whereby it was established that the $^{123}$I-labeled compound had an $R_f$ of 0.82.

A radioactivity distribution was determined utilizing a chromatogram scanner using a sodium iodide crystal-counting system peaked to the 159 keV emission of I-123. The location of the mass of material was determined by observing the chromatogram under ultraviolet light at 254 um. As seen under the UV light, 100% of the activity was found to migrate to the above given $R_f$ which is the same as that of the starting material.

The ethanol was then evaporated to half volume and the reaction mixture taken up with a vehicle comprising a mixture of equal volumes of two solutions, the first solution comprising 50 parts ethanol, 250 parts propylene glycol and 7.5 parts benzyl alcohol. The second solution comprised 200 parts water and 50 parts of said first solution having dissolved therein 200 mg/l disodium edetate, and buffered to a pH of 7 with an acetic acid/sodium acetate buffer. The resulting solution was filtered through a bed of silver chloride prepared by passing a 2% by weight aqueous solution of silver nitrate through a filter paper disc followed by normal saline and the above described vehicle. A 3 um membrane filter was incorporated downstream from the silver chloride impregnated disc.

EXAMPLE 12

Bioassays were performed utilizing compounds from the foregoing examples labeled with I-123 in accordance with the method described in Example 11. Female Sprague-Dawley rats weighing approximately 150 g. were anesthetized with sodium pentobarbital and were injected in a tail vein with from 0.05 to 1.0 mCi (in a volume of 0.2 to 0.5 ml) of the I-123-labeled compound. Two specimens were utilized for each test.

The animals were sacrificed at 5 minutes post injection, the tails discarded and the amount of activity in various organs determined. Each organ was counted at a standardized geometry with a thallium iodide-activated sodium iodide crystal scintillation counter adjusted for the 159 keV emission of I-123. The organs were also weighed to one thousandth of a gram and the activity calculated as a percent of administered dose per gram organ weight.

The ratio of brain-to-blood activity was calculated as a percent of administered dose per gram. The results are reported in the following table. The important determinations are the amount of activity in the brain and the brain/blood ratio. The amount of activity in the stomach is related to loss of the I-123-label. For comparative purposes, I-123 antipyrine was utilized as a standard.

TABLE

| I-123 Compound Corresponding to Example No. | Percent Dose/g. at 5 min. | | | Ratio | | Percent Dose in Stomach |
|---|---|---|---|---|---|---|
| | Blood | Brain | Heart | Brain/Blood | Heart/Blood | |
| 2 | 2.06 | 0.29 | 1.22 | 0.14 | 0.59 | 0.81 |
| 5 | 1.67 | 0.73 | 1.12 | 0.43 | 0.67 | 0.79 |
| 6 | 1.69 | 0.34 | 1.02 | 0.20 | 0.60 | 0.92 |
| 7 | 1.73 | 0.44 | 1.13 | 0.25 | 0.65 | 1.46 |
| 8 | 2.39 | 0.19 | 1.21 | 0.08 | 0.51 | 0.77 |
| 9 | 1.61 | 0.31 | 1.02 | 0.19 | 0.63 | 0.93 |
| 10 | 1.01 | 0.12 | 0.54 | 0.12 | 0.53 | 0.92 |
| $I_{123}$-iodoantipyrine[a] | 1.26 | 0.61 | 0.98 | 0.48 | 0.78 | 2.23 |

[a]Prepared according to J. Nucl. Med., 17, 1093 (1976).

I claim:

1. A method of imaging the brain comprising intravenously injecting into a patient an effective amount of a composition comprising a compound of the formula

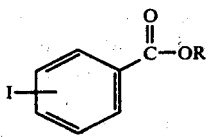

wherein I is a radioisotope of iodine, and R is selected from the group consisting of alkyl, aryl, substituted aryl, aralkyl, a polyhydric alcohol, and a 5- or 6-membered heterocyclic ring, in a carrier suitable for intravenous injection and scanning the brain with a scintiscanning means.

2. A method in accordance with claim 1 wherein I is iodine-123.

3. A method in accordance with claim 1 wherein I is ortho to the ester group.

4. A method in accordance with claim 1 wherein said compound is I-123 ethyl-o-iodobenzoate.

5. A method in accordance with claim 1 wherein said compound is I-123 glyceryl-o-iodobenzoate.

6. A method in accordance with claim 1 wherein said compound is I-123 benzyl-o-iodobenzoate.

* * * * *